(12) United States Patent
Waddell

(10) Patent No.: US 10,319,569 B2
(45) Date of Patent: *Jun. 11, 2019

(54) SELF CLEANING ION GENERATOR DEVICE

(71) Applicant: Charles Houston Waddell, Roanoke, VA (US)

(72) Inventor: Charles Houston Waddell, Roanoke, VA (US)

(73) Assignee: Global Plasma Solutions, Inc., Savannah, GA (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/297,638

(22) Filed: Oct. 19, 2016

(65) Prior Publication Data
US 2017/0040149 A1    Feb. 9, 2017

Related U.S. Application Data

(63) Continuation-in-part of application No. 14/971,050, filed on Dec. 16, 2015, now Pat. No. 9,925,567.
(Continued)

(51) Int. Cl.
*H01J 37/32* (2006.01)
*B03C 3/74* (2006.01)
(Continued)

(52) U.S. Cl.
CPC .......... *H01J 37/32862* (2013.01); *A61L 9/22* (2013.01); *B01D 53/323* (2013.01); *B08B 1/007* (2013.01); *B08B 1/04* (2013.01); *H01J 37/32541* (2013.01); *H01J 37/32568* (2013.01); *H01T 23/00* (2013.01); *B01D 2257/708* (2013.01); *B01D 2257/91* (2013.01); *B01D 2258/06* (2013.01); *B01D 2259/4508* (2013.01); *B01D 2259/818* (2013.01)

(58) Field of Classification Search
CPC combination set(s) only.
See application file for complete search history.

(56) References Cited

U.S. PATENT DOCUMENTS

| | | | |
|---|---|---|---|
| 4,734,580 A * | 3/1988 | Rodrigo | H01T 23/00 250/324 |
| 4,757,422 A | 7/1988 | Bossard et al. | |

(Continued)

OTHER PUBLICATIONS

"Products" Web Page, http://www.gpshvac.com/index.php?option=com_content&view=article&id=11&itemid=93, 1 page, Apr. 29, 2013, retrieved from Internet Archive Wayback Machine, https://web.archive.org/web/20130429232411/http://www.gpshvac.com/index.php?option=com_content&view=article&id=11&Itemid=93 on Jan. 20, 2017.
(Continued)

*Primary Examiner* — Robert A Hopkins
*Assistant Examiner* — Sonji Turner
(74) *Attorney, Agent, or Firm* — Seth L. Hudson; Clements Bernard Walker, PLLC

(57) ABSTRACT

The present invention provides methods and systems for a self-cleaning ion generator that includes a self-cleaning ion generator device that includes a bottom portion, a top portion, and a sidewall, and at least one electrode extending from the top portion, and a cleaning apparatus for cleaning the at least one electrode.

16 Claims, 13 Drawing Sheets

Related U.S. Application Data

(60) Provisional application No. 62/094,684, filed on Dec. 19, 2014.

(51) Int. Cl.
    *B08B 1/00*     (2006.01)
    *B08B 1/04*     (2006.01)
    *H01T 23/00*     (2006.01)
    *A61L 9/22*     (2006.01)
    *B01D 53/32*     (2006.01)

(56) References Cited

U.S. PATENT DOCUMENTS

| | | | |
|---|---|---|---|
| 4,809,127 A | 2/1989 | Steinman et al. | |
| 5,741,352 A | 4/1998 | Ford et al. | |
| 5,768,087 A * | 6/1998 | Vernitskiy | H01T 23/00 |
| | | | 15/256.5 |
| D434,523 S * | 11/2000 | Ford | D23/364 |
| 6,464,754 B1 * | 10/2002 | Ford | B03C 3/38 |
| | | | 361/226 |
| 6,680,033 B2 | 1/2004 | Ishii | |
| 6,850,403 B1 | 2/2005 | Gefter et al. | |
| 7,177,133 B2 | 2/2007 | Riskin | |
| 7,256,979 B2 | 8/2007 | Sekoguchi et al. | |
| 7,408,759 B2 * | 8/2008 | Gefter | H01T 23/00 |
| | | | 361/230 |
| 7,497,898 B2 | 3/2009 | Sato et al. | |
| 7,716,772 B2 * | 5/2010 | Shih | B08B 1/04 |
| | | | 15/21.1 |
| 8,106,367 B2 | 1/2012 | Riskin | |
| 8,564,924 B1 * | 10/2013 | Waddell | H01T 23/00 |
| | | | 361/231 |
| 8,724,286 B2 * | 5/2014 | Uchida | H01T 23/00 |
| | | | 361/230 |
| 8,861,168 B2 * | 10/2014 | Waddell | H01T 23/00 |
| | | | 361/231 |
| 8,957,571 B2 | 2/2015 | Riskin | |
| D754,314 S | 4/2016 | Ellis et al. | |
| 2018/0169711 A1 * | 6/2018 | Waddell | B01D 53/32 |

OTHER PUBLICATIONS

"RGF Environmental Air Purification Technologies—Guardian Air HVAC Cell" Web Page, http://www.airstarsolutions.com/Pages/RGFguardian.aspx,3 pages, Aug. 20, 2012, retrieved from Internet Archive Wayback Machine, https://web.archive.org/web/20120820000149/http://www.airstarsolutions.com/Pages/RGFguardian.aspx on Jan. 20, 2017.

* cited by examiner

SELF CLEANING ION GENERATOR DEVICE

CROSS REFERENCE TO RELATED PATENT APPLICATION

The current application is a continuation-in-part of U.S. patent application Ser. No. 14/971,050, filed on Dec. 16, 2015 and titled "Self-Cleaning Ion Generator," which claims the benefit of the earlier priority filing date of the provisional application, Ser. No. 62/094,684, that was filed on Dec. 19, 2014.

FIELD OF THE INVENTION

The present invention relates generally to the field of air treatment, and more particularly to the treatment of air using ionization that has a self-cleaning mechanism for cleaning the electrodes of an ionization device without having to remove the device from the conduit or duct.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering air for these and other applications. It is to the provision of improved systems and methods meeting these needs that the present invention is primarily directed.

BRIEF SUMMARY OF THE INVENTION

According to an embodiment of the present invention a self-cleaning ion generator device includes a housing having at least an arcuate portion, at least one electrode extending from the housing, and a cleaning apparatus for cleaning the at least one electrode.

According to another embodiment of the present invention, a self-cleaning ion generator device wherein the housing includes a top portion and a bottom portion.

According to yet another embodiment of the present invention, a self-cleaning ion generator device that includes a cleaning apparatus powered by a motor for rotation during periodic intervals.

According to yet another embodiment of the present invention, a self-cleaning ion generator device wherein the housing has a top portion, a bottom portion, and a mounting portion engaging the bottom portion and the top portion.

According to yet another embodiment of the present invention, a self-cleaning ion generator device that includes a bottom portion selectively secured to a mounting portion, and the top portion is selectively secured to the mounting portion.

According to yet another embodiment of the present invention, a self-cleaning ion generator device that includes at least one electrode selectively secured to an ion generator disposed within the housing.

According to yet another embodiment of the present invention, a self-cleaning ion generator device that includes at least two electrodes spaced apart and extending from the housing.

According to yet another embodiment of the present invention, a self-cleaning ion generator device that includes a collar extending from the device for mounting the device.

According to yet another embodiment of the present invention, a self-cleaning ion generator device that includes at least one electrode that consists of a plurality of bristles extending therefrom.

According to yet another embodiment of the present invention, a self-cleaning ion generator device that includes a housing having a top portion, a bottom portion, and a sidewall, a mounting portion engaged to the housing, at least one electrode extending from the housing, and a cleaning apparatus for cleaning the at least one electrode.

According to yet another embodiment of the present invention, a self-cleaning ion generator device that includes an ion generator housed within the housing for receiving the at least one electrode.

According to yet another embodiment of the present invention, a self-cleaning ion generator device that includes a motor housed within the housing and rotationally engaged to the cleaning apparatus for activating the cleaning apparatus at a predetermined interval.

According to yet another embodiment of the present invention, a self-cleaning ion generator device that includes a circuit board within the housing According to yet another embodiment of the present invention, a method of producing ions that includes providing an ion generator with at least one electrode and having a top portion, a bottom portion, and a sidewall, and a cleaning apparatus for cleaning the at least one electrode.

According to yet another embodiment of the present invention, a method of producing ions that includes providing a motor and cleaning head for self-cleaning.

According to yet another embodiment of the present invention, a method of producing ions that includes providing a motor for rotationally engaging the cleaning apparatus.

According to yet another embodiment of the present invention, a method of producing ions that includes a collar for mounting the device to the conduit.

According to yet another embodiment of the present invention, a method of producing ions that includes mounting the device after a prefilter and before a cooling coil.

According to yet another embodiment of the present invention, a method of producing ions wherein the self-cleaning device is integral to the ion device structure or designed for post installation to an ion device with at least one electrode to provide self-cleaning.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
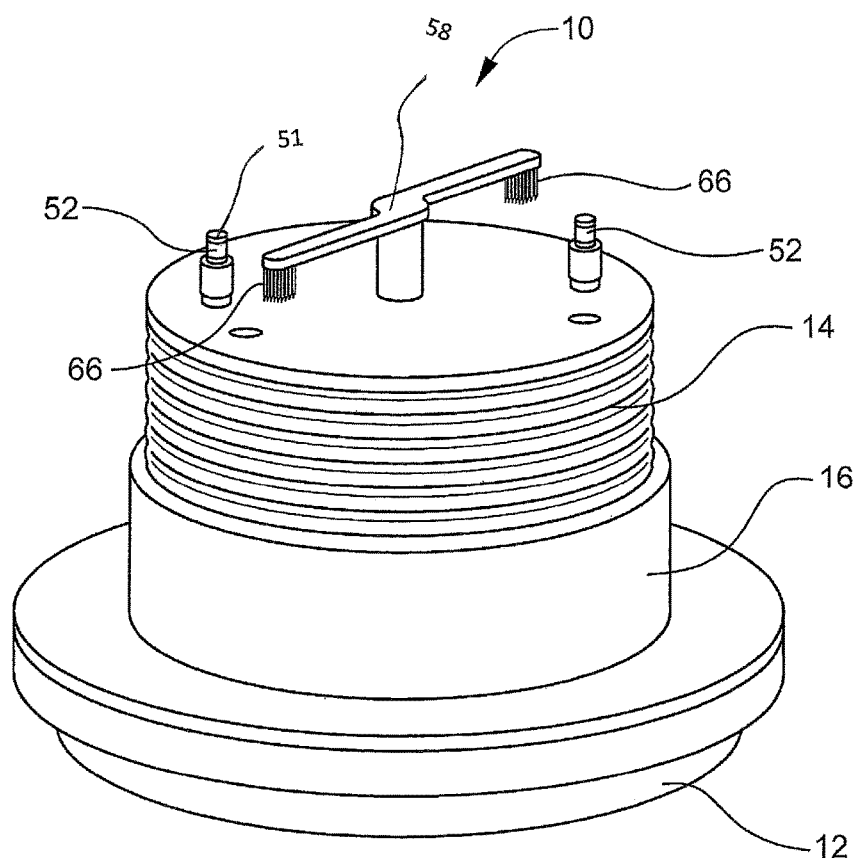
FIG. 1 is a side view of the self-cleaning ion generator device.

Referring now specifically to the drawings, a self-cleaning ion generator device is illustrated in FIG. 1 and is shown generally at reference numeral 10. The device 10 includes a housing having a bottom portion 12 and a top portion 14. The top portion 12 and the bottom portion 14 may be engaged to each other, or alternatively, a mounting portion 16 may be used to engage the top portion 12 and the bottom portion 14. The top portion 14 may be selectively secured to the bottom portion 12, or alternatively, the top portion 14 may be selectively secured to the mounting portion 16 and the bottom portion 12 may be selectively secured to the mounting portion 16.

The bottom portion 12 may be generally circular and extends outward to an outer edge with the bottom portion 12 having an exterior side and an interior side. An outer ring 18 extends generally upwardly from the outer edge of the bottom portion 12 to an upper edge. Inside the interior of the outer ring 18, an inner ring 20 extends generally upwardly from the interior side of the bottom portion to an upper edge. A cavity 22 is formed within the interior of the inner ring 20. The outer ring 18 and inner ring 20 are in a spaced-apart relationship and creating a space between the outer ring 18 and inner ring 20. A least one key 24 is positioned within this space.

The bottom portion 12 contains at least one tab 26 containing a centrally located bore 28. The centrally located bore 28 is designed to fit overtop a corresponding bore within a base mount or the like that can be positioned within a duct.

Figure 7:
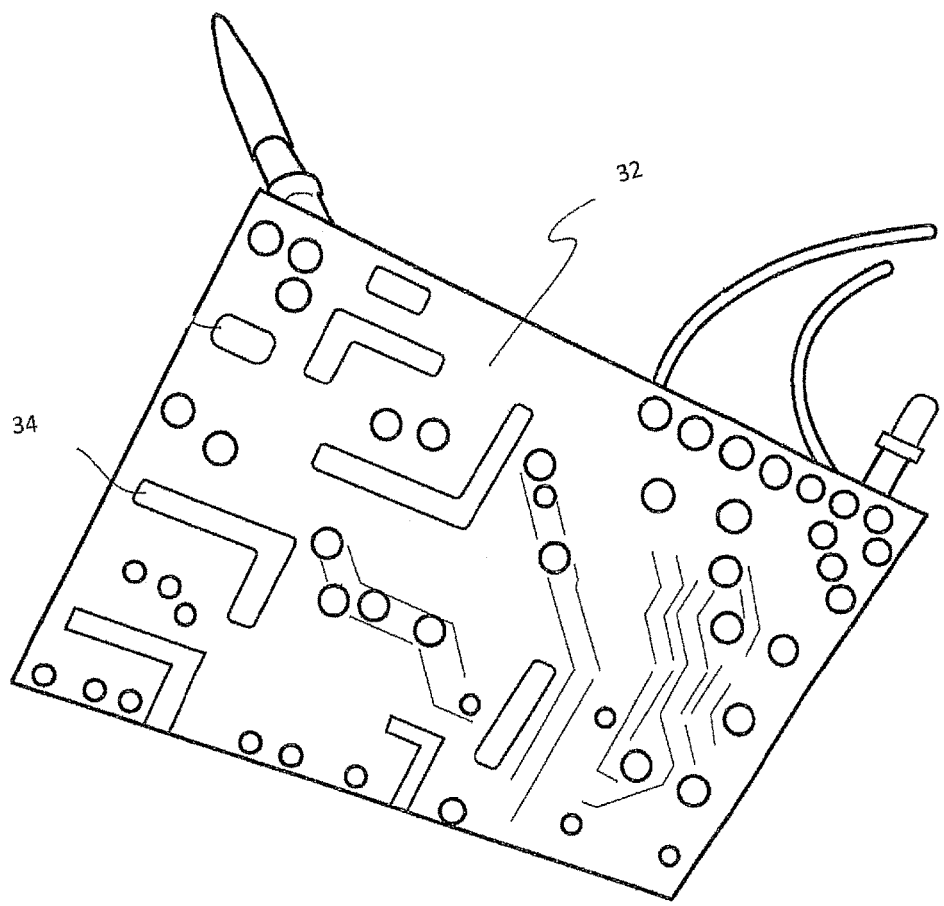
FIG. 7 is a perspective view of one embodiment of the circuit board.
Figure 8:
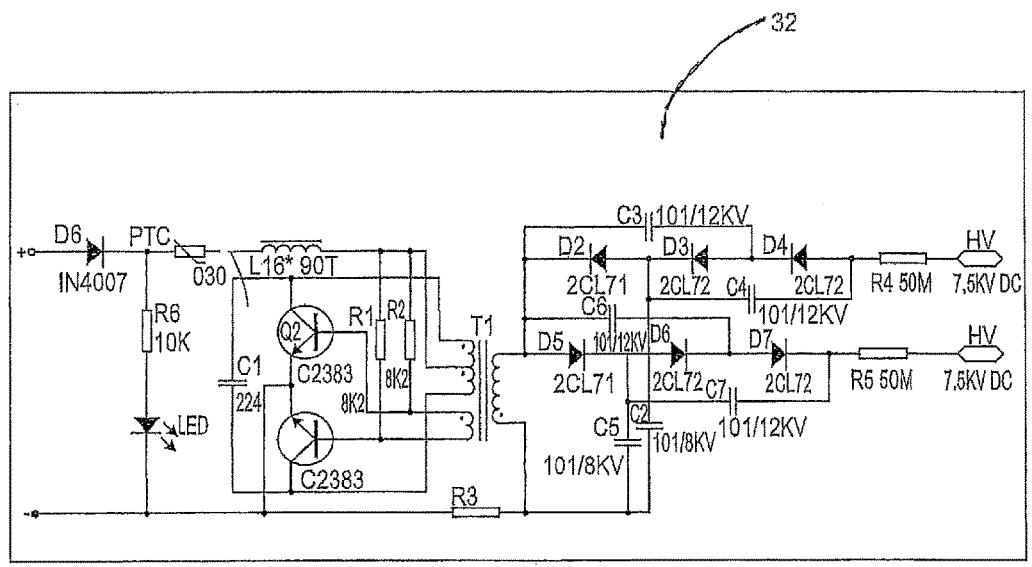
FIG. 8 is a schematic diagram of the circuit board.

A terminal 30 is positioned within the cavity 22 of the bottom portion 12. The terminal is electrically and communicatively coupled to a circuit board 32, as illustrated in FIG. 7, that is contained within the cavity 22 of the bottom portion 12 and may have a circuit diagram as illustrated in FIG. 8. The circuit board 32 is not continuous and has air gaps 34 contained therein. The purpose of the air gaps 34 is to prevent the high voltage from jumping to the low voltage area, and preventing the low voltage from jumping to the high voltage area. The cavity 22 may be filled with an epoxy.

The circuit board 32 may include a power supply source for providing power to the device 10. The circuit board 32 is communicatively coupled to an ion generator 36 to produces ions. The power supply provides the electricity to power the ion generator 36, and thus, produce ions. Additionally, the circuitry also includes a timing circuit for timing a DC stepper motor 38 that engages or is activated at a predetermined time.

The mounting portion 16 includes a preferably hollow column 40 surrounded by an outwardly extending collar 42. The mounting portion 16 has an upper portion, bottom portion, inner surface, and outer surface. The inner surface may be internally threaded. The collar 42 extends outwardly from the outer surface and in close proximity to the bottom portion of the hollow column 40. Preferably, the collar 42 is positioned in such a way that a portion of the column 40 extends beyond a bottom surface of the collar 42 and a larger portion of the column 40 extends beyond a top surface of the collar 42. At least one key 44 is positioned on the bottom surface of the collar 42 that mates in a selectively secured relationship with the at least one key 24 contained in the space of the bottom portion 12. In another alternative embodiment, the space on the bottom portion 12 may contain two or more keys 24 and the bottom surface of the collar 42 may contain two or more keys 44 for mating with the two or more keys 24 on the bottom portion 12 for forming a selectively secured arrangement between the mounting portion 16 and bottom portion 12. The collar 42 may contain a plurality of ribs disposed thereon.

The inner ring 20 of the bottom portion 12 fits within the interior of the hollow column 40 of the mounting portion 16 for forming a selectively secured arrangement between the bottom portion 12 and the mounting portion 16. The at least one key 44 positioned on the bottom surface of the collar 42 mates in a selectively secured relationship with the at least one key 24 contained in the space of the bottom portion 12 for forming this selectively secured arrangement.

The top portion 14 contains an upper surface that extends outwardly to an outer edge and a rim that extends downwardly from the outer edge. A cavity is formed within the upper surface and rim of the top portion. The rim contains an inner surface and an outer surface, wherein the outer surface may contain external threads. The external threads of the top portion 14 correspond with the internal threads of the mounting portion 16 for forming a selectively secured arrangement between the top portion 12 and mounting portion 16.

Figure 2:
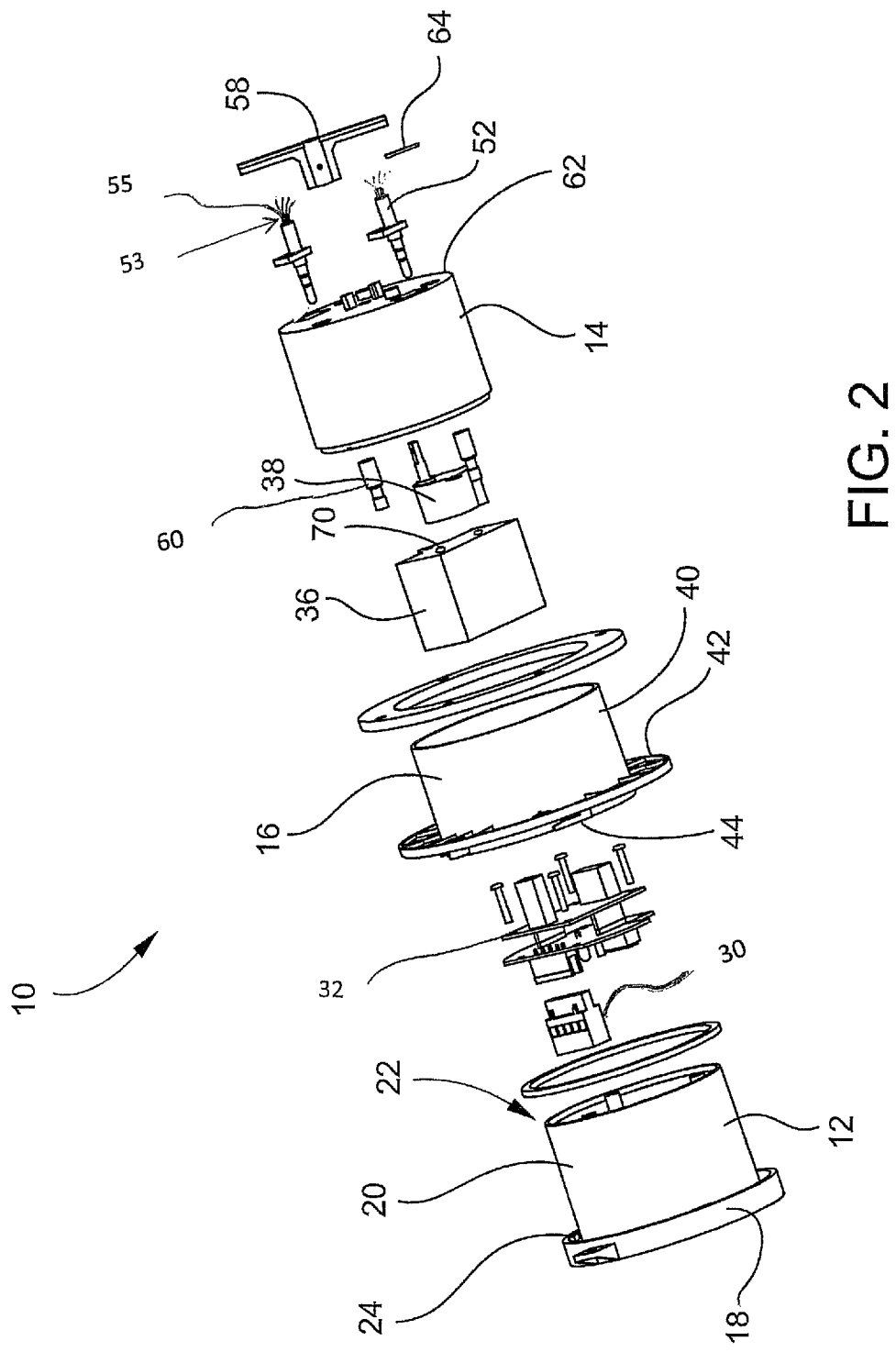
FIG. 2 is an exploded view of the self-cleaning ion generator device.

The upper surface of the top portion 14 may contain at least one bore 50, and as illustrated in FIGS. 1 and 2, the upper surface of the top portion 14 may contain at least two bores 50. The bores extend through the upper surface. An ion terminal 52 extends through the at least one bore 50. In one embodiment, a first high voltage wire or electrode 51 extends from the ion generator 36 through a bore 50 and a second high voltage wire or electrode 51 extends extending from the ion generator 36 through another bore 50. In one embodiment, a hollow column 40 encircles the bore 50 and extends perpendicularly upward from the top portion 14 of the device 10 for providing support to the first or second high voltage wire or electrode 51. A hollow column 40 may encircle the bore 50 containing the first high voltage wire or electrode 51, and a hollow column 40 may encircle the bore 50 containing the second high voltage wire or electrode 51. The end of the first and second high voltage wire or electrode 51 may contain a brush 53 that contains a plurality of bristles 55 that extend outwardly away from the brush 53. The brush 53 and its bristles 55 may be made of any material that conducts electricity and the combination of the brush 53 with its bristles 55 and the high voltage wire or electrode 51 may be collectively referred to herein as an electrode 51. In one embodiment, the bristles 55 of the brush 53 are composed of a thermoplastic polymer imbedded with conductive material that allows the polymer to conduct electricity. For example, the bristles 55 of the brush 53 may be composed of polypropylene or polyethylene and impregnated with carbon. Generally, the bristles 55 of the brush 53 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles 55 of the brush 53. The brushes 53 are replaceable and allowed to be easily disengaged and new bristles 55 may be inserted and retained.

In one embodiment, the brush 53 is engaged to the end of the high voltage wires or electrode 51. The brush 53 may be crimped to the end of the high voltage wires extending outwardly from the device 10. In another embodiment, the brush 53 is engaged to the end of the high voltage wires extending outwardly from the device 10 by heat shrink. In one embodiment, the high voltage wires come off the transformer on the circuit board 32 at 6500 volts, wherein the first high voltage wire and associated brush deposits a stream of negative ions into the surrounding air and the second high voltage wire and associated brush 53 deposits positive ions into the surrounding air.

In another alternative embodiment, the ion terminal 52 may be replaceable. As illustrated in FIG. 2, the ion terminal 52 may have an upper portion and a lower portion, wherein the upper portion and lower portion are separated by a retention ring 54. The retention ring 54 may be selectively secured to the top portion 14 by a fastening means, such as a screw or the like. Ions flow out of the ion terminal 52 through electrodes 51 positioned on the uppermost section of the upper portion. In the embodiments illustrated herein, the upper portion contains a brush 53 (as described above) that allows ions to flow from the brushes 53.

The lower portion of the ion terminal 52 fits within the bore 50 of the top portion 14 and fits within a bore 70 of the ion generator 36. The ion generator 36 contains a female portion for releasably receiving the male portion of the lower portion of the ion terminal 52. The retention ring 54 retains the ion terminal 52 within the top portion 14. After the ion terminal 52 has been used for a predetermined period of time or when the ion terminal 2 suffers a reduction in effectiveness, the ion terminal 52 may be removed from the top portion 14 and ion generator 36 and replaced with a new one. The lower portion of the ion terminal 52 extends into the cavity of the top portion 14 and into the ion generator 36.

Figure 4:
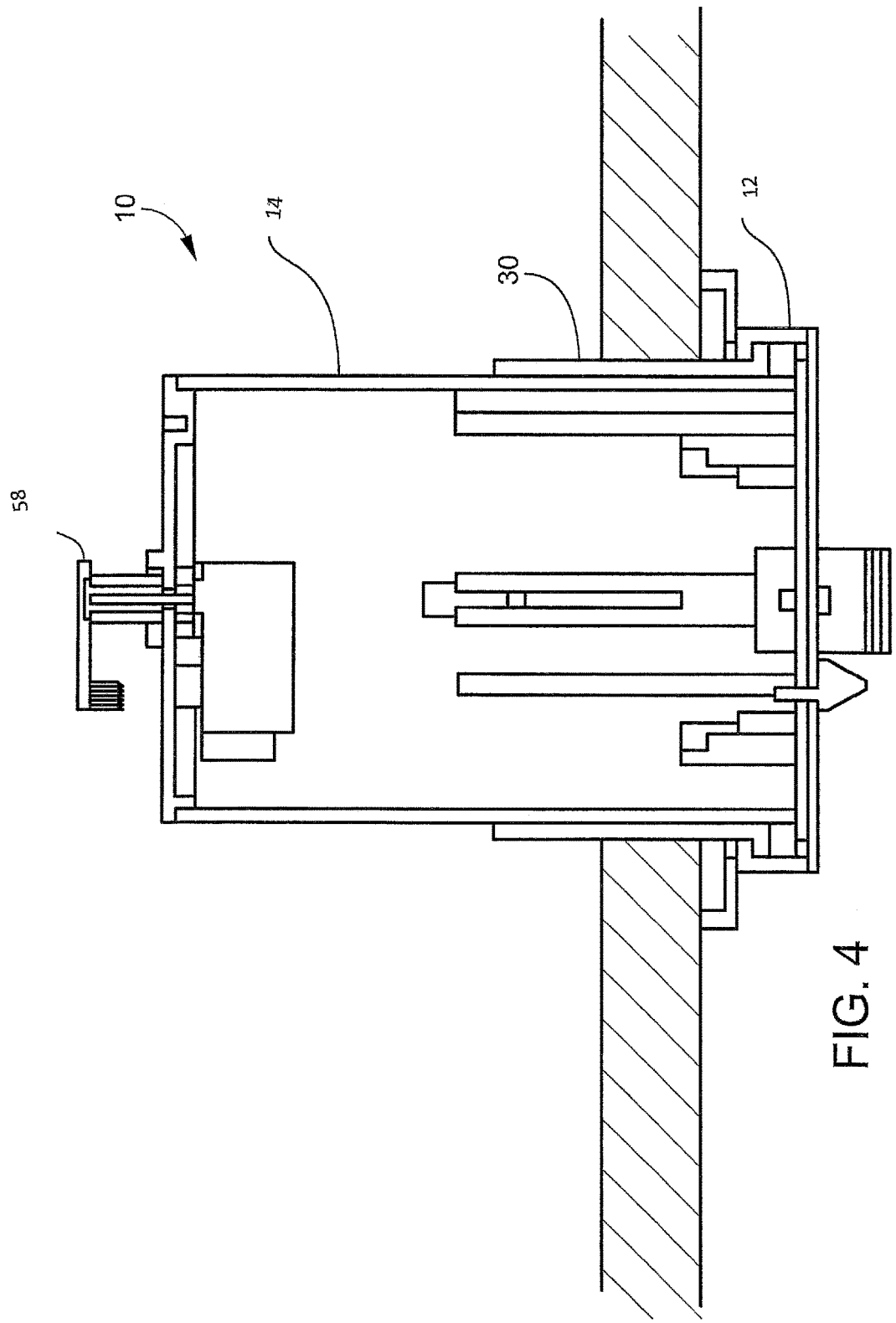
FIG. 4 is a cut-away side view of the self-cleaning ion generator device.

A stepper motor 38 is positioned below the top portion, as shown in FIGS. 2 and 4. The stepper motor 38 is used to power a cleaning apparatus 58. The stepper motor 38 contains a terminal for receiving a power supply for providing power to the stepper motor 38. A rotational arm 60 extends generally outward from the stepper motor 38 and through a generally centrally located bore 62 that extends from the upper surface to the bottom surface of the top portion 14. The cleaning apparatus 58 is releasably engaged to the rotational arm 60 extending through the bore 62 of the top portion 14. As illustrated, the cleaning apparatus 58 is releaseably engaged to the rotational arm 60 by a fastening means, such as a bolt 64.

The cleaning apparatus 58 may be T-shaped, or in an alternative embodiment L-shaped. As illustrated in FIG. 2, the T-shaped cleaning apparatus 58 has a horizontal portion and a vertical portion. The vertical portion contains a hollow shaft that is releasably engaged to the rotational arm 60. The horizontal portion extends outwardly from the vertical portion and contains a cleaning head 66 on each end of the vertical portion. The cleaning head 66 may contain any device that may clean the electrode 51 or brushes 53 of the ion terminal 52.

The cleaning apparatus 58 is powered by the DC stepper motor 38 operationally connected to a timing circuit that activates the cleaning apparatus 58 at a predetermined interval. By way of example only, the cleaning apparatus 58 may be activated between every 12 to 24 hours. In one alternative embodiment and as illustrated, the cleaning apparatus 58 is "S" shaped or curved. In other words, when the cleaning apparatus 58 is viewed from above, the cleaning apparatus 58 has an "S" shaped or curved appearance, preventing both cleaning heads 66 from contacting the electrodes 51 or brushes 53 from ion terminal 52 at the same time. While the cleaning apparatus 58 is activated, the device 10 ceases to produce ions, thus preventing any loose particles from sticking to the opposite polarity brush 53. The cleaning apparatus 58 may be straight, such as a bar as illustrated in FIG. 2, or any other shape as desired by the user.

Figure 5:
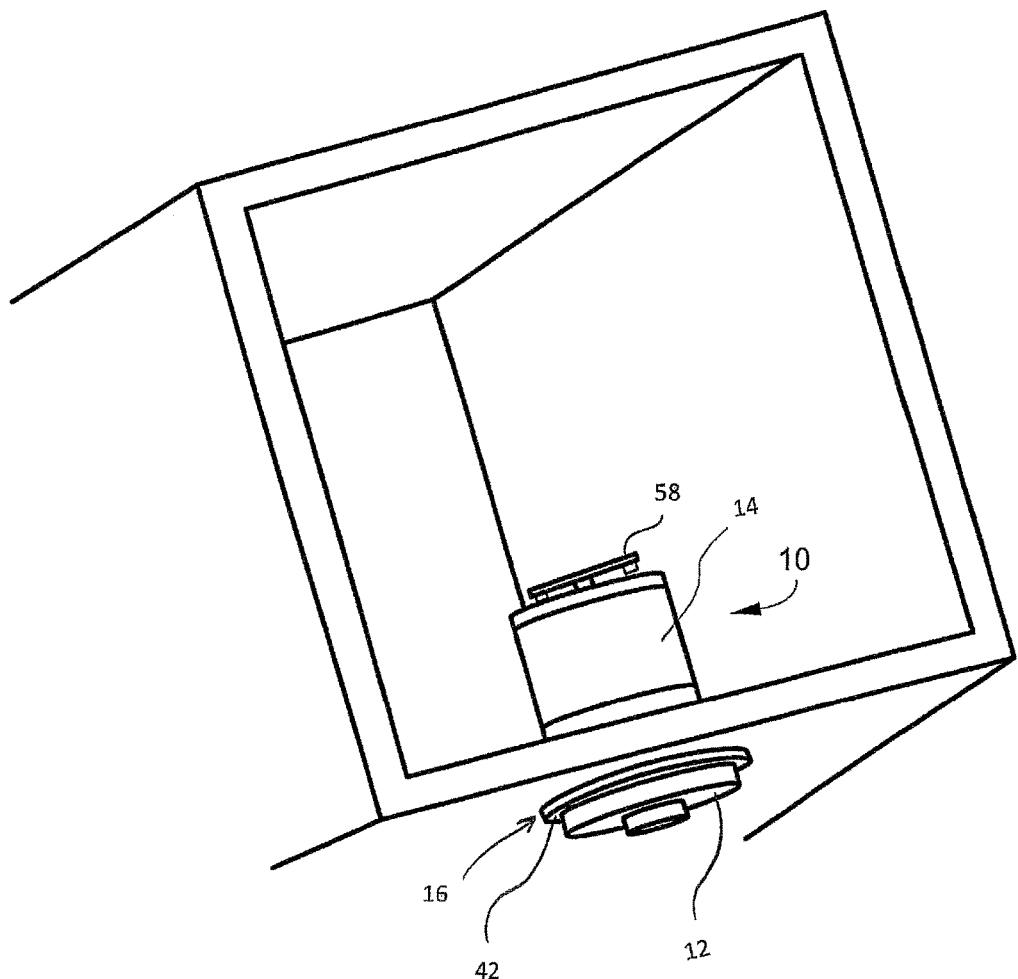
FIG. 5 is a side perspective view of the self-cleaning ion generator device installed in an duct.
Figure 9:
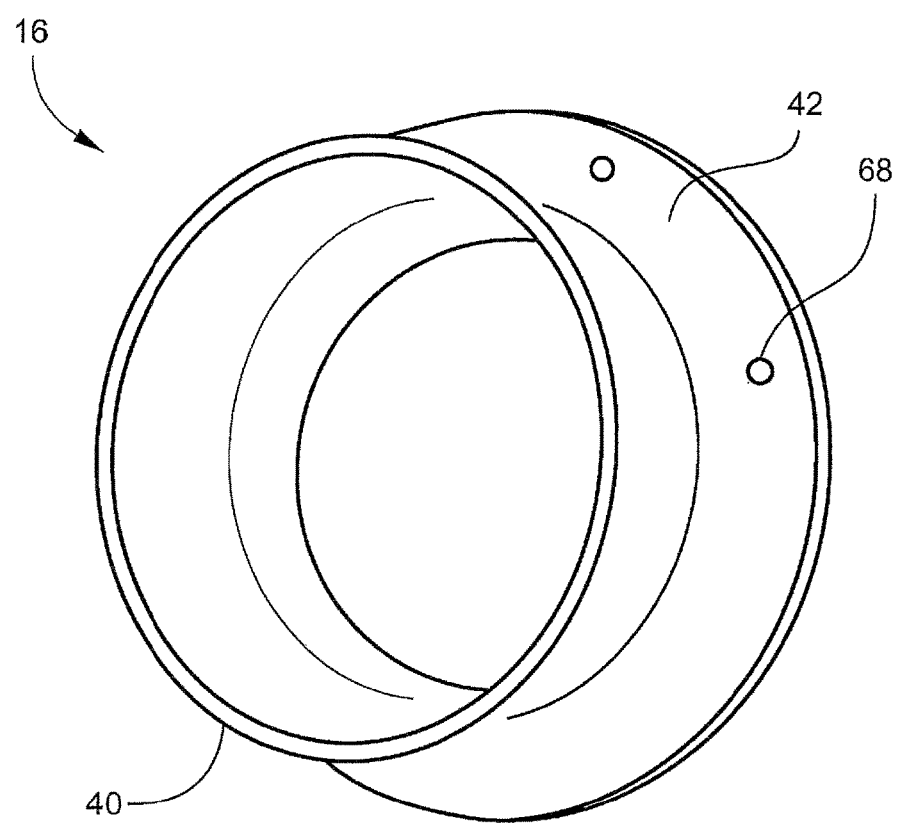
FIG. 9 is a perspective view of the mounting portion.

The collar 42 of the mounting portion 16 is engaged to a duct, as shown in FIG. 5. The top surface of the collar 42 is engaged to the exterior side of a duct. The collar 42 may contain at least one mounting hole 68 that extends between the top surface to the bottom surface, as illustrated in FIG. 9 for receiving a fastening means for engaging the device 10 to the duct. Fastening means may include a screw, bolt, self-tapping sheet metal screws, spring loaded wing nuts with bolts, and the like. When mounted to a duct or other conduit, the top portion 14 extends within the duct or conduit with the electrodes 51 or brushes 53 extending within the duct and conduit, releasing ions with the duct or conduit. The bottom portion 12 is visible on the exterior of the duct. Preferably, the device 10 is mounted after a prefilter and before the cooling coil in an HVAC system. Alternatively, the device 10 may be mounted on any conduit with air flow, a supply air duct, or a return air duct. The device 10 should be mounted so that air flows over the electrodes 51 or brushes, such as air my flow through the goal posts on a football field.

As mentioned above, the bottom portion 12 of the device 10 contains at least one key 24 that corresponds with at least one key 44 on bottom surface of the collar 42 of the mounting portion 16. The mounting portion 16 is inserted into the bottom portion 12 and the rotation of the bottom portion 12 of the device within the mounting portion 16 allows the keys (24, 44) to mate in a selectively secured arrangement, forming a selectively secured arrangement between the bottom portion 12 and the mounting portion 16. The keys (24, 44) allow the bottom portion 12 to be selectively secured to the mounting portion 16 in a selectively secured arrangement with less than a quarter turn of either the bottom portion 12 with respect to the mounting portion 16, or vice versa.

Figure 3:
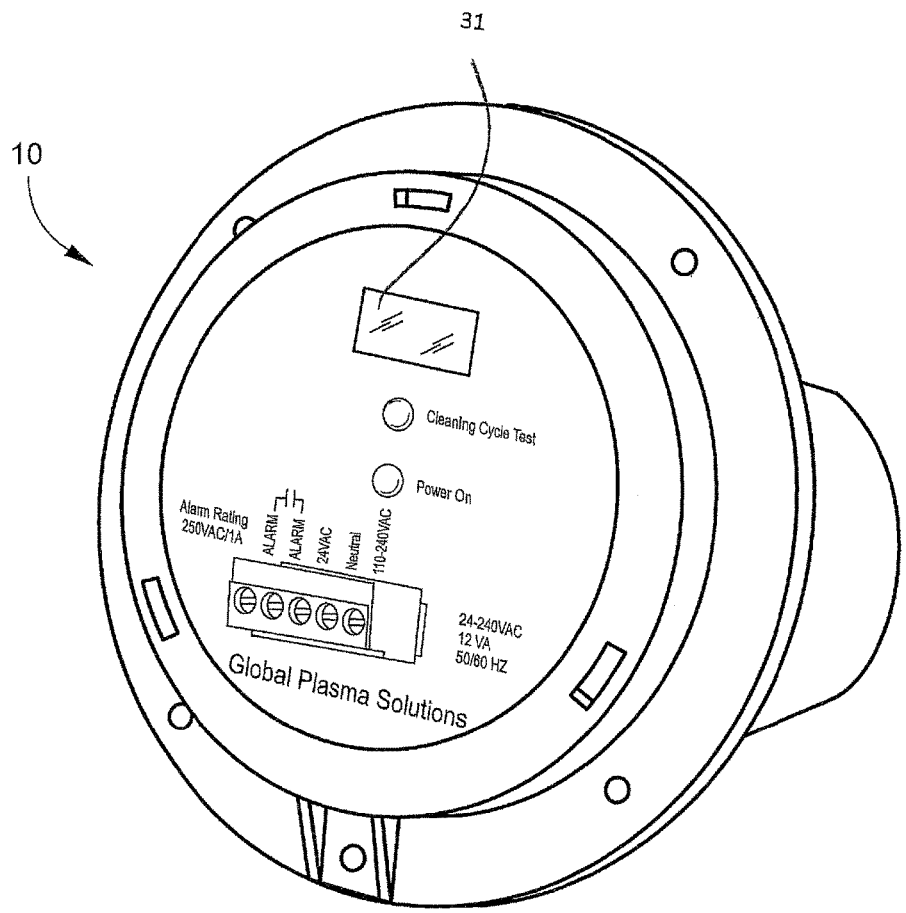
FIG. 3 is a bottom view of the self-cleaning ion generator device.

In an alternative embodiment of the present invention, the device 10 includes an alarm feature, including alarm contacts, that are communicatively coupled to a building management system that sends a signal to the building management system if ions are not produced by the device 10. The building management system then sends an alert informing a user that the device 10 is not producing ions. A test button may also be located on the device 10 to check the motor status during preventive maintenance and a light, such as an LED light, may be illuminated, indicating a cleaning test is being conducted. A light, such as an LED light, may be positioned on the bottom portion 12 that is illuminated and indicating power is being supplied to the device 10, as shown in FIG. 3

The device 10 may produce approximately equal amounts of positive and negative ions, regardless of airflow velocity or other conditions such as humidity or temperature. In example forms, the device 10 produces positive ions and negative ions in a concentration of at least about $10^9$ ions/second, and operates on 24 VAC, 110 VAC or 200 VAC to 240 VAC without the use of an external transformer. In alternate embodiments, the device generates negative ions only, or positive ions only, or generate negative ions and positive ions in unequal quantities. The device 10 optionally utilizes nano-electronic components allowing the device to be very compact, requiring less than 1 watt/ion generator module, for example less than 0.5 watts/ion module, and in further examples less than 0.36 watts per ion module. The bottom portion 12 may contain terminals extending therefrom for connecting the 24 VAC, 110-240 VAC, and neutral input.

The device 10 may be positioned and secured in place within a conduit or the housing of the air handler unit, such as a duct, such that the electrodes are aligned generally perpendicularly to the direction of the airflow across the device 10, to prevent recombination of the positively charged ions with the negatively charged ions.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

During use, once power is provided to the device 10, the device 10 initiates an internal check on all systems. After initializing and the check has confirmed all systems are operational, a display 31 on the bottom portion 12 will blink "on" and include a visible meter of how many days the device 10 has been powered. After each day of being powered, the display 31 will add a number to the display 31 indicating the number of days the device 10 has been powered. The bottom portion 12 also contains a test button that when pushed, initiates a cleaning cycle of the device 10, causing the cleaning apparatus 58 to rotate and cleaning the ion terminals 52.

Figure 6:
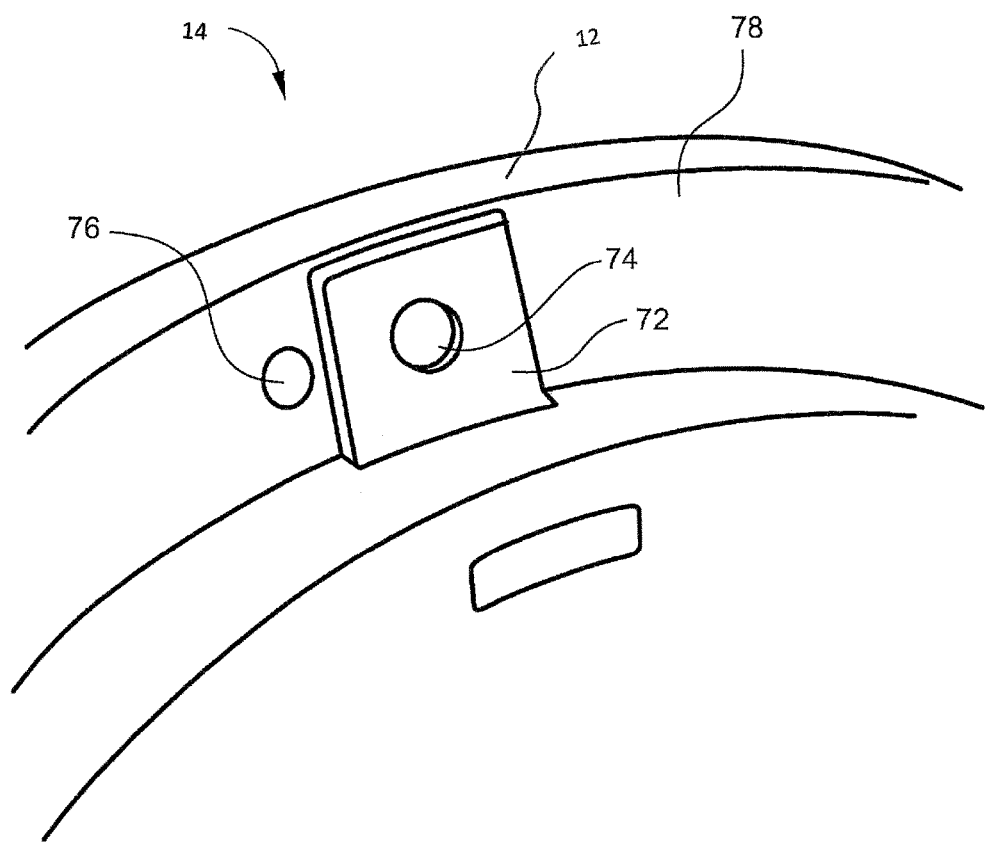
FIG. 6 is a top perspective view of the locking tab.

In an alternative embodiment as illustrated in FIG. 6, the bottom portion 12 contains at least one tab 72 containing a centrally located bore 74. The centrally located bore 74 fits overtop a corresponding bore 76 within a base mount 78 that may be positioned within the duct for easy mounting. The base mount 78 may be affixed to a hole formed within the conduit or duct for selectively receiving the device 10.

In an alternative embodiment, the cleaning apparatus 58 may be added to an existing ion generator, or in other words a modular cleaning apparatus that can be added to an existing ion generator. In this embodiment, the cleaning apparatus 58 is attached to the ion generator near the electrode 51 or electrodes 51, such that the cleaning head(s) 66 of the cleaning apparatus may come in contact with the electrodes 51 of the ion generator. A motor 38 may be communicatively coupled to the cleaning apparatus 58 for activating the cleaning apparatus as a predetermined interval. The cleaning apparatus 58 and function is described above.

Figure 10:
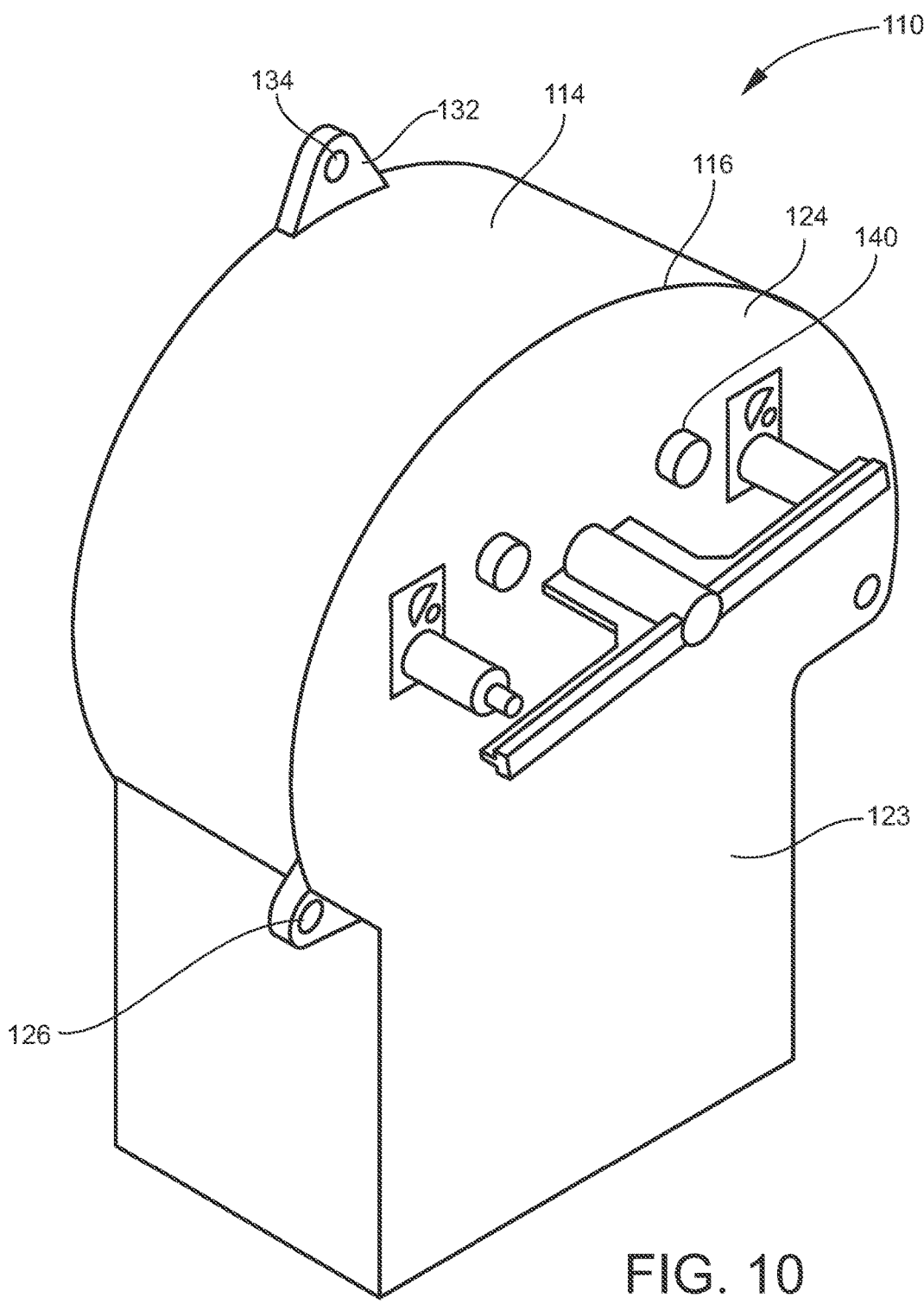
FIG. 10 is a perspective view of an alternative embodiment of the self-cleaning ion generator device.
Figure 11:
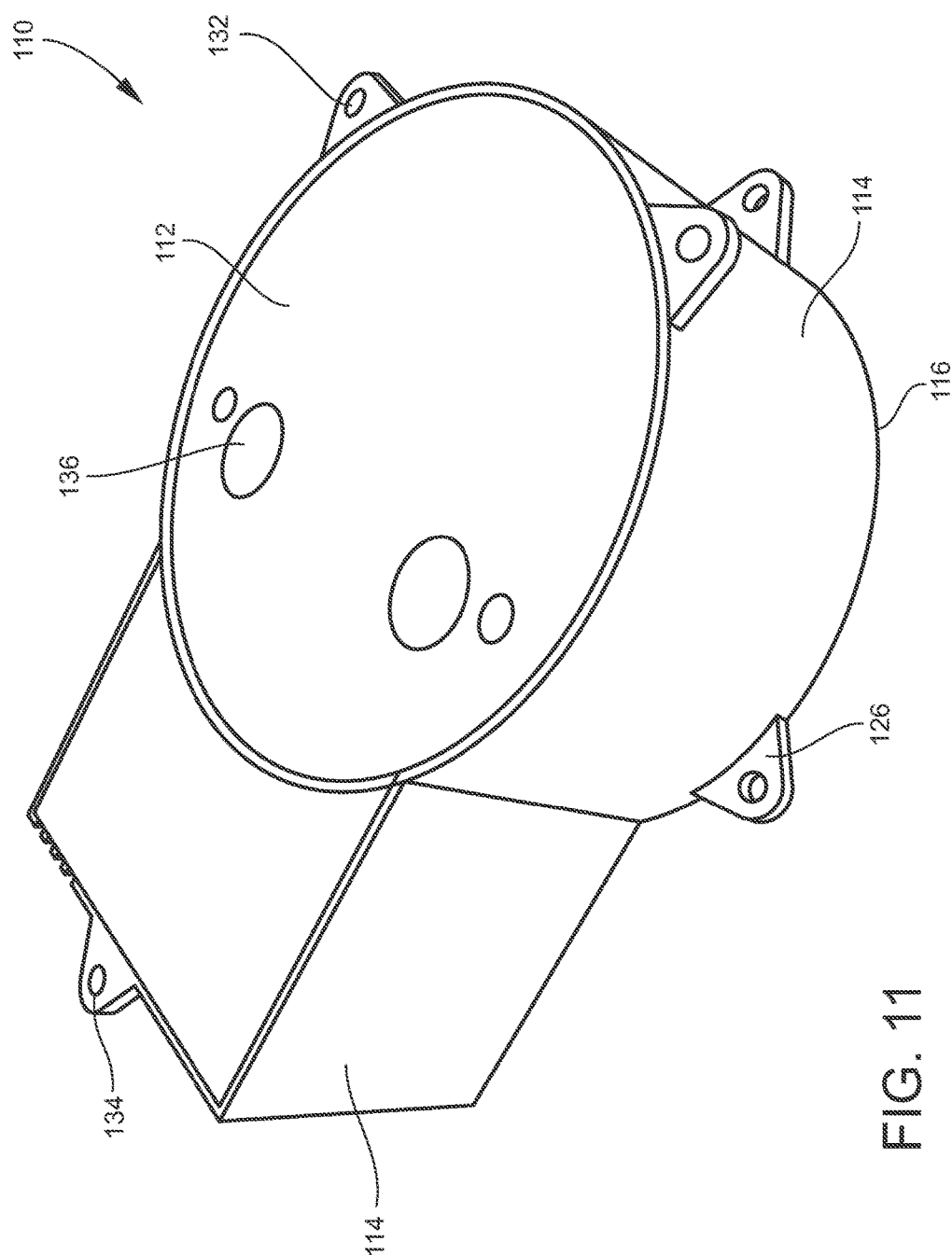
FIG. 11 is a bottom perspective view of the self-cleaning ion generator device.
Figure 12:
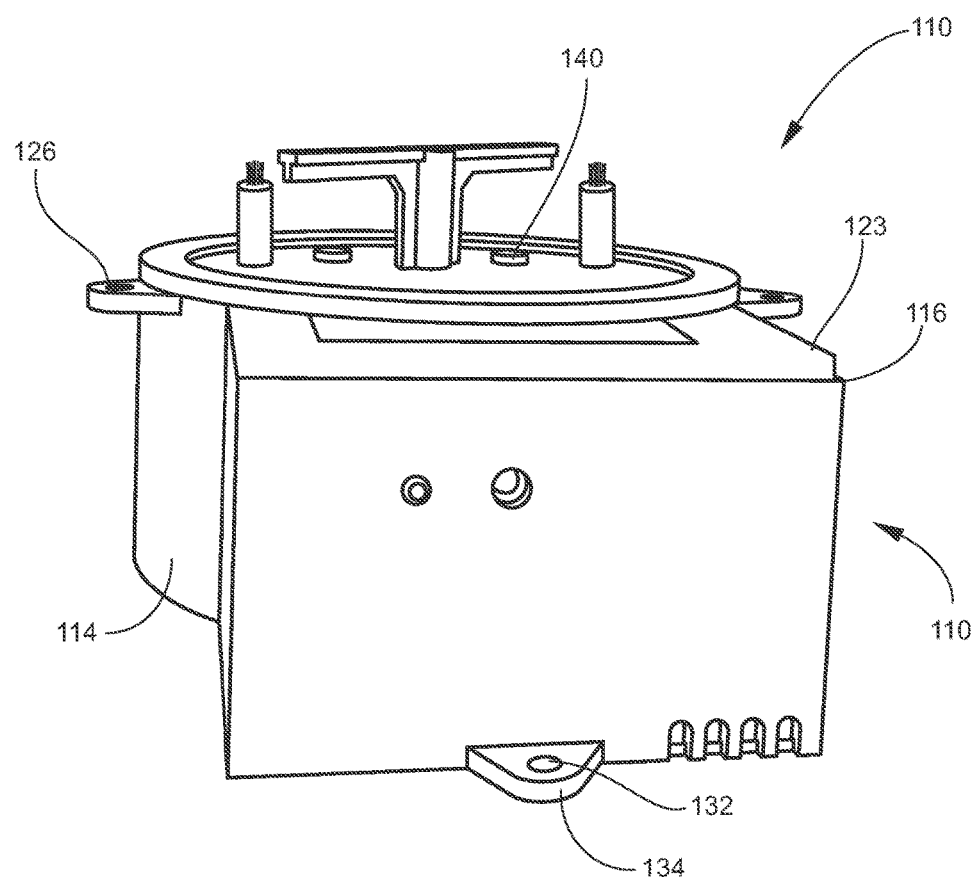
FIG. 12 is a side perspective view of the self-cleaning ion generator device.

In an alternative embodiment, as illustrated in FIGS. 9, 10, and 11, the ionization device is shown generally at reference numeral 110. The device 110 includes a base 112 that extends to an outer edge. A sidewall 114 extends from the outer edge of the base 112 to an upper edge 116. The sidewall 114 has an inner and outer sidewall surface, respectively, forming an interior storage compartment. A top portion 124 is engaged to the upper edge 116 and enclosing the interior storage compartment 122.

The base 112 has an arcuate upper portion and a generally square or generally rectangular bottom portion and has a bottom side and a top side. In other words, the base 112 has a generally keyhole shape. The sidewall 114 extending upward generally conforms to the shape of the base and has an arcuate upper portion and a generally square or generally rectangular bottom portion. The upper edge 116 of the sidewall 114 surrounds the generally cylindrically shaped sidewall 114. The top portion 124 that is engaged to the upper edge 116 has an arcuate upper portion and a generally square or generally rectangular bottom portion.

The base 112 may be integral with the sidewall 114. Alternatively, the base 112 and sidewall 114 may be separate, wherein a first end of the sidewall 114 is disposed adjacent the outer edge of the base 112, and the second end of the sidewall 114 is disposed adjacent the top portion 124. The base 112 and sidewall 114 may be engaged to each other by an attachment device, such as an adhesive, screw, bolt, or the like. Likewise, the top portion 124 may be integral to the second end of sidewall 114. Alternatively, the top portion 124 and sidewall 114 may be engaged to each other by an attachment device, such as an adhesive, screw, bolt, or the like.

At least one upper retention flange 126 extends from the sidewall 114. The upper retention flange 126 extends outwardly from the sidewall 114 and generally planar to the upper edge 116. The upper retention flange 126 contains an upper portion, a bottom portion, and two side portions. The upper retention flange 126 also contains a bore that extends from the upper portion to the lower portion for allowing a retention device, such as a screw, bolt, or the like, to be inserted therethrough and selectively securing or engaging the upper retention flange 126 to a wall, duct, or the like.

As illustrated, the device 110 may have two upper retention flanges 126 that are in a spaced-apart relationship. As shown, the upper retention flanges 126 are disposed on opposed sides of the sidewall 114 for selectively securing or engaging the device 110 to a wall, duct, or the like. The upper retention flanges 126 engage the duct, and allow the device 110 to be mounted to the duct.

The device 110 may also contain at least one bottom retention flange 132. The bottom retention flange 132 extends outward from the outer edge of the base 112. The generally triangular shape of the bottom retention flange 132 allows the bottom retention flange 132 to selectively secure or engage the device 110 to a confined space within a wall, duct, or the like. The bottom retention flange 132 provides stability and support for the device 110. The bottom retention flange 132 has an upper portion, a bottom portion, and two side portions. A bore 134 extends from the upper portion to the bottom portion of the bottom retention flange 132 for allowing a retention device, such as a screw, bolt, or the like, to be inserted therethrough and selectively securing or engaging the bottom retention flange 132 to a wall, duct, or the like. The bottom retention flange 132 is engaged to the exterior side of a duct, allowing at least the top portion 124 and a portion of the sidewall 114 to be inserted into the duct and flow of air.

As illustrated, the device 110 may have two bottom retention flanges 132 that are in a spaced-apart relationship. As shown, the bottom retention flanges 132 are disposed on opposed sides of the sidewall 114 for selectively securing or engaging the device 110 to a wall, duct, or the like. The upper retention flange 126 and bottom retention flange 132 are offset from each other. In other words, the placement of the upper retention flange 126 is not "over top" or above the bottom retention flange 132. As illustrated, the upper retention flanges 126 are offset by 45 degrees from the bottom retention flanges 132.

The base 112 of the device 110 may also contain at least one magnet 136 on the bottom side. The at least one magnet 136 may be generally circular in shape, and the base 112 of the device 110 contains a correspondingly shaped bore disposed on the bottom side for receiving the at least one magnet 136. As illustrated, the base 112 contains two bores for receiving one magnet 136 in each bore. The at least one magnet 136 may be recessed within the bore and flush with the bottom side of the base 112. The device 110 may contain two magnets 136 on the bottom of the base 112. The magnets 136 are designed to selectively secure the device 110 to a wall, duct, or the like. The cleaning apparatus as shown on the device 110 is disclosed above.

The top portion 124 may be covered by foam, or alternatively, the top side of the top portion 124 may be covered by a closed cell foam gasket 123 that acts as an air seal when mounted to a duct or the like. An LED 140 may also be disposed on the top portion 124 of the device 110.

Figure 13:
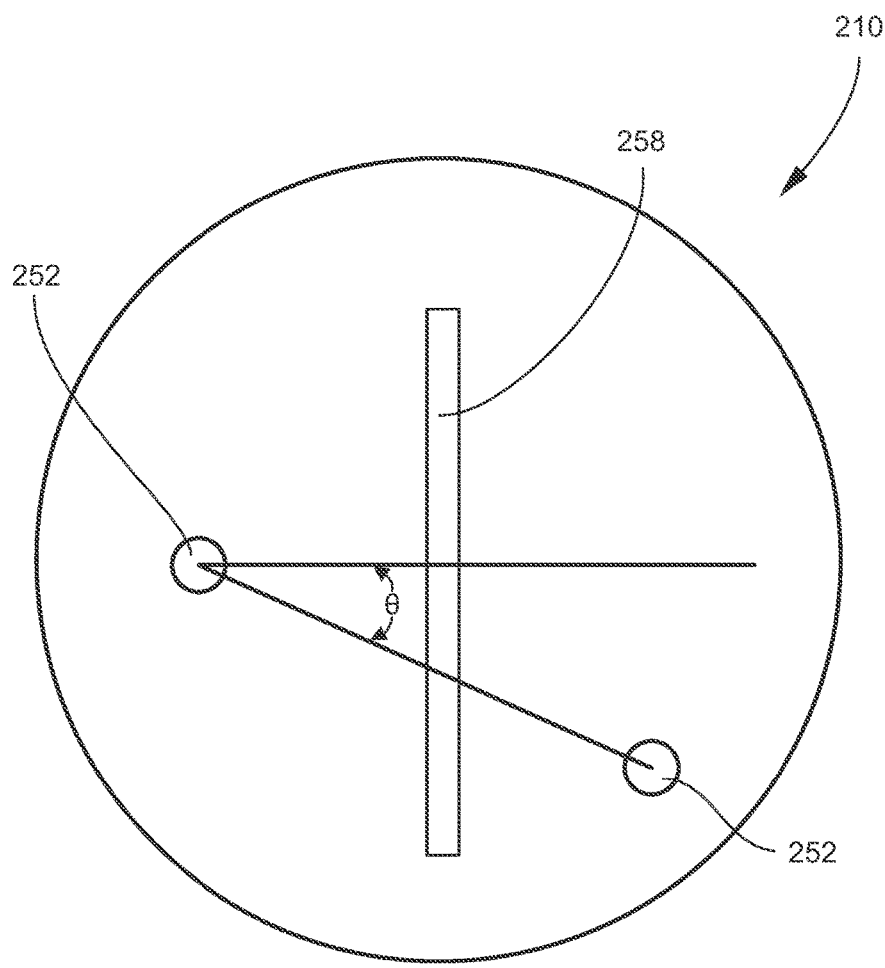
FIG. 13 is a top view of an alternative arrangement of the ion terminals.

As illustrated in FIG. 13, the ion terminals 252 may be offset from one another. In other words, instead of the ion terminals 252 being across from each other, the ion terminals 252 are offset or set apart by a predetermined degree. Preferably, the predetermined degree e is preferably between about 1° to about 89° and more preferably between about 10° and about 70°. The cleaning apparatus 258 is able to clean the ion terminals even with the offset or set apart arrangement.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A self-cleaning ion generator device, comprising:
    a base that extends to an outer edge having a keyhole shape, the base has an upper portion and a bottom portion, the upper portion has an arcuate shape and the bottom portion is square shaped, a sidewall that extends from the outer edge of the base to an upper edge forming a storage compartment within the base and sidewall; and a top portion engaged to the upper edge of the sidewall enclosing the storage compartment;
    two electrodes extending from the top portion; and
    a cleaning apparatus for cleaning the electrodes.

2. The self-cleaning ion generator device of claim 1, wherein the cleaning apparatus is powered by a motor for rotation during periodic intervals.

3. The self-cleaning ion generator device of claim 1, wherein the electrodes are selectively secured to an ion generator disposed within the storage compartment.

4. The self-cleaning ion generator device of claim 1, further comprising a collar extending from the device for mounting the device.

5. The self-cleaning ion generator device of claim 1, further comprising at least one cleaning head disposed on the cleaning apparatus for cleaning the electrodes.

6. The self-cleaning ion generator device of claim 1, wherein the electrodes consists of a brush with a plurality of bristles extending therefrom.

7. A self-cleaning ion generator device, comprising:
    a base that extends to an outer edge having a keyhole shape, the base has an upper portion and a bottom portion, the upper portion has an arcuate shape and the bottom portion is square shaped, a sidewall extends from the outer edge of the base to an upper edge forming a storage compartment within the base and sidewall, and a top portion having a top side and engaged to the upper edge of the sidewall enclosing the storage compartment; two electrodes extending from the housing;
    a cleaning apparatus for cleaning the electrodes;
    the base contains two circular bores for receiving two circular magnets, wherein the magnets are flush with the bottom side of the base; and
    a foam covering the top side of the top portion.

8. A self-cleaning ion generator device according to claim 7, further comprising an ion generator housed within the storage compartment for receiving the electrodes.

9. A self-cleaning ion generator device according to claim 7, further comprising a motor housed within the housing and rotationally engaged to the cleaning apparatus for activating the cleaning apparatus at a predetermined interval.

10. A self-cleaning ion generator device according to claim 7, further comprising a display for providing a visual indication indicating the device is operating.

11. A self-cleaning ion generator device according to claim 7, further comprising two bottom retention flanges extending outward from the outer edge of the base and two upper retention flanges that extend outwardly from the sidewall, wherein the upper retention flanges and lower retention flanges are offset from each other.

12. A method of producing ions, comprising:
    providing a base that extends to an outer edge having a keyhole shape, the base has an upper portion and a bottom portion, the upper portion has an arcuate shape and the bottom portion is square shaped, a sidewall extends from the outer edge of the base to an upper edge forming a storage compartment within the base and sidewall, and a top portion having a top side engaged to the upper edge of the sidewall enclosing the storage compartment, two electrodes extend from the top portion, a cleaning apparatus for cleaning the electrodes, the base contains two circular bores for receiving two circular magnets, wherein the magnets are flush with the bottom side of the base, and a foam covering the top side of the top portion; and positioning the top portion within a conduit such that the two electrodes are aligned generally perpendicular to the direction of airflow within the conduit.

13. The method of producing ions according to claim 12, further comprising providing a collar for mounting the ion generator.

14. The method of producing ions according to claim 12, further comprising mounting the ion generator after a pre-filter and before a cooling coil in the conduit.

15. A method of producing ions according to claim 12, further comprising an integral motor and cleaning head for self cleaning.

16. The method of producing ions according to claim 12, wherein the self-cleaning device is integral to the ion device structure or designed for post installation to an ion device with the electrodes providing the self-cleaning.

* * * * *